United States Patent [19]

Ohta et al.

[11] Patent Number: 5,610,139
[45] Date of Patent: Mar. 11, 1997

[54] ANTIMICROBIAL COMPOSITIONS AND PHARMACEUTICAL PREPARATIONS THEREOF

[75] Inventors: Michio Ohta; Nobuo Kato, both of Nagoya, Japan

[73] Assignee: Seikagaku Corporation, Tokyo, Japan

[21] Appl. No.: 375,165

[22] Filed: Jan. 18, 1995

Related U.S. Application Data

[63] Continuation of Ser. No. 38,162, Mar. 26, 1993, abandoned.

[30] Foreign Application Priority Data

Mar. 30, 1992 [JP] Japan .................................... 4-103511

[51] Int. Cl.$^6$ .................................................. A61K 38/10
[52] U.S. Cl. .............................. 514/13; 514/12; 514/15; 530/325; 530/326; 530/327
[58] Field of Search ............................. 514/2–4, 12–13, 514/21

[56] References Cited

U.S. PATENT DOCUMENTS 4,863,902  9/1989  Amagase .................................. 514/12

FOREIGN PATENT DOCUMENTS

| 0384410 | 8/1990 | European Pat. Off. . |
| 0502198 | 9/1992 | European Pat. Off. . |
| WO89/01492 | 2/1989 | WIPO . |

OTHER PUBLICATIONS

Alpert, "Limulus Antilipopolysaccharide Factor Protects Rabbits From Meningococcal Endotoxin Shock", The J. of Infectious Diseases, 165: 494–500 (1992).
Matsuzaki, "Interactions of an Antimicrobial Peptide, Tachyplesin I, With Lipid Membranes", Biomembranes, 1070: 259–264 (1991).
Murakami, "Direct Virus Inactivation of Tachyplesin I and Its Isopeptides From Horseshoe Crab Hemocytes", Chemotherapy, 37: 327–333 (1991).
Ohta, "Mechanisms of Antibacterial Action of Tachyplesins and Polyphemusins, a Group of Antimicrobial Peptides Isolated From Horseshoe Crab Hemocytes", Antimicrobial Agents & Chemotherapy, 36: (1992).
Shigenaga, "Antimicrobial Tachyplesin Peptide Precursor", The J. of Biological Chemistry, 265: 21350–21354 (1990).
Usawattanakul, "Tachypleus Lysate Test For Endotoxin In Patients With Gram Negative Bacterial Infections", The Southeast Asian J. of Tropical Medicine And Public Health, 10: 13–17 (1979).
Zasloff, "Antibiotic Peptides As Mediators of Innate Immunity", Current Opinion in Immunology, 4: 3–7 (1992).
Blanchi, "Pharmacodynamics", Chemical Abstracts, 77:14809–14810 (1972).
JP Patent No. JP 2167230 (abstract).
JP Patent No. JP 4082840 (abstract).
JP Patent No. JP 2270897 (abstract).
JP Patent No. JP 2207098 (abstract).
JP Patent No. JP 2152987 (abstract).
JP Patent No. JP 2053799 (abstract).
Kawano, "Antimicrobial Peptide, Tachyplesin I, Isolated From Hemocytes of the Horseshoe Crab (Tachypleus tridentatus)", The J. of Biological Chemistry, 265:15365–15367 (1990).
Liang, "Studies on Limulus Amoebocyte Lysate", The J. of Biological Chemistry, 255:5586–5590 (1980).
Matsuzaki, "Interactions of an Antimicrobial Peptide, Tachyplesin I, With Lipid Membranes", Biochimica et biophysica Acta, 1070: 259–264 (1991).
Minetti, "Purification and Characterization of an Endotoxin–binding Protein with Protease Inhibitory Activity from Limulus Amebocytes", The J. of Biological Chemistry, 266: 20773–20780 (1991).
Miyata, "Antimicrobial Peptides, Isolated From Horshoe Crab Hemocytes, Tachyplesin II, and Polyphemusins I and II: Chemical Structures And Biological Activity", J. Biochem., 106:663–668 (1989).
Nakamura, "Tachyplesin, a Class of Antimicrobial Peptide from Hemocytes of the Horseshoe Crab (Tachypleus tridentatus)", The J. of Biological Chemistry, 263:16709–16713 (1988).
Shieh, "Synthesis and Properties of Tachyplesin I, a Lipopolysaccharide–Binding Peptide, From Tachypleus tridentatus", Febs Letters, 252: Nos. 1, 2, pp. 121–124 (Jul. 1989).
Nester et al., Microbiology, Holt Rinehart and Winston, Inc., New York, 1973, p. 190.
The Merck Index, 9th ed., Martha Windholz, Editor, Merck and Co., Inc. Rahway, N.J. 1976, p. 245 Entry No. 1911.
The Merck Index, 9th ed., Merck & Co. Inc. Rahway, N.J. 1976, p. 261, entry No. 2040.

Primary Examiner—David Lukton
Attorney, Agent, or Firm—Testa, Hurwitz & Thibeault, LLP

[57] ABSTRACT

Antimicrobial compositions which are effective against methicillin-resistant *Staphylococcus aureus* organisms (MRSAs) contain peptides isolated from horseshoe crabs combined with one or more β-lactam antibiotics and/or chloramphenicol antibiotics. The compositions exhibit synergistic bactericidal effects against MRSAs at low concentrations, and can be used as defensive agents against opportunistic infections.

12 Claims, 1 Drawing Sheet

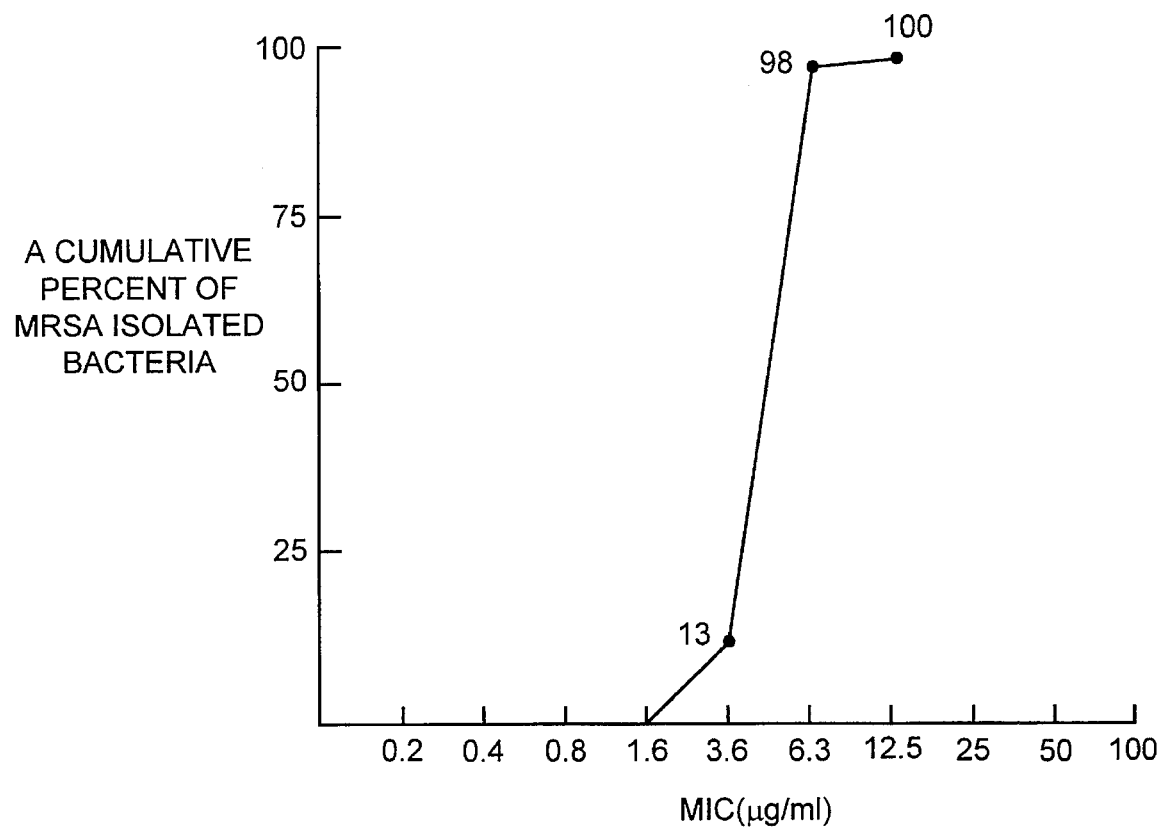

5,610,139

ANTIMICROBIAL COMPOSITIONS AND PHARMACEUTICAL PREPARATIONS THEREOF

This is a continuation of application Ser. No. 08/038,162 filed on Mar. 26, 1993 now abandoned.

BACKGROUND OF THE INVENTION

1. Field of the Invention

This invention relates to antimicrobial compositions, furthermore relates to antimicrobial agents containing the composition as active ingredient particularly useful for the prevention and treatment of opportunistic infectious diseases.

2. Description of the Prior Art

Methicillin-resistant *Staphylococcus aureus* (hereinafter abbreviated as MRSA) includes *Staphylococcus aureus* strains that are resistant to various antimicrobial agents such as methicillin, cephem antibiotics, and so on. The strains have recently been noted as pathogens of nosocomial infections such as opportunistic infections, and countermeasures to these infectious diseases of nowadays are serious problems for medical care. Some MRSAs are resistant not only to cephem antibiotics but also to chloramphenicol antibiotics.

Antimicrobial activity of peptides isolated from the hemocytes of horseshoe crabs against Gram positive and negative bacteria, and fungi have been known. However, these peptides do not exhibit sufficient antimicrobial activity by single administration. For example, the minimum inhibitory concentration (MIC) against *Staph. aureus* is reported to be 3.1–6.2 µg/ml. Doses of these antimicrobial peptides sufficient to induce antimicrobial activity causes toxic side effect. The peptides are expensive and not easily available as they are isolated from natural horseshoe crab. Therefore, antimicrobial peptides isolated from the hemocytes of horseshoe crab could not easily be used as antimicrobial agents.

SUMMARY OF THE INVENTION

The present invention relates to an antimicrobial agent against MRSAs which is effective at a low dose with less toxicity. The inventors found that combinations of antimicrobial peptides isolated from said hemocytes of horseshoe crab and a β-lactam antibiotic or chloramphenicol antibiotic effectively inhibit the growth of Gram positive bacteria including MRSAs and Gram negative bacteria at small doses.

Thus, one object of the present invention is to provide antimicrobial compositions particularly useful for medical treatment, which inhibit the growth of not only MRSAs but also other Gram positive and negative bacteria at low concentrations with less toxicity. So far, there are few agents that effectively inhibit the growth of MRSAs.

The other object of the present invention is to provide agents for the prevention and treatment of opportunistic infections by the activity shown above.

The present invention is provided to solve above mentioned problems and relates to antimicrobial compositions comprising antimicrobial peptides derived from horseshoe crab, their derivatives or pharmaceutically acceptable salts and a β-lactam antibiotic or chloramphenicol antibiotic.

The present invention further relates to antimicrobial compositions containing said compositions, particularly agents for the prevention and treatment of opportunistic infectious diseases.

BRIEF DESCRIPTION OF THE DRAWINGS

FIG. 1 shows antibacterial activity of tachyplesin I against 55 strains of clinically isolated MRSAs.

DETAILED DESCRIPTION OF THE PREFERRED EMBODIMENT

The antimicrobial peptides of the present invention derived from horseshoe crab include tachyplesin I, tachyplesin II, tachyplesin III, polyphemusin I, polyphemusin II and gigasin II. These peptides found in hemocytes of horseshoe crab are basic peptides having 17–18 amino acids and have four cysteines in their molecules forming two intramolecular S—S bonds to give cyclic structures. The peptides possess antimicrobial activity against Gram positive and negative bacteria but also have relatively high MICs. Small differences between their MICs and toxic concentrations made their clinical application very difficult.

The peptides of the present invention include not only natural antimicrobial peptides derived from horseshoe crab but also derivatives which have been modified for example, by substituting or deleting one or more amino acids or elongating by adding one or more amino acids; whereby said derivatives exhibit similar antimicrobial activity (hereinafter abbreviated as derivatives). These derivatives include peptides in which basic and/or aromatic amino acids with other basic and/or aromatic amino acids, respectively.

Above mentioned antimicrobial peptides can be extracted from the hemocytes of horseshoe crab such as *Limulus polyphemus* available in U.S.A., *Tachypleus tridentatus* available in China and Japan, *Tachypleus gigas* available in Thailand and Malaya Peninsula and *Carcinoscorpius rotundicauda* available in Thailand and Malaya Peninsula by known methods. These peptides can be obtained by known peptide synthetic methods such as solid phase synthesis and liquid phase synthesis, or by genetic engineering methods using transformed or transfected microorganisms and animal cells having gene DNA coding for said peptides. Furthermore, said peptides may be acid amide form at the C-terminal amino acid.

The antimicrobial peptides isolated from horseshoe crab contain many basic amino acids such as arginine and lysine and may form salts with acids.

The present invention can utilize such pharmaceutically acceptable salts as hydrochloride, sulfate, nitrate, phosphate, formate, acetate, lactate, oxalate, maleate, fumarate, succinate, trifluoroacetate, p-toluenesulfonate, methanesulfonate, and etc.

The β-lactam antibiotics used in the present invention include cephalosporins and penicillins. Any known antibiotics can be used for the present invention. Cephalosporin antibiotics include cefazolin, cephalexin, cefamandole, cefoxitin, cefmetazole, cefotaxime and cefotetan, and penicillin antibiotics such as ampicillin, hetacillin, talampicillin, bacampicillin and carbenicillin.

Furthermore, chloramphenicol may be used.

The antimicrobial compositions of the present invention composed of antimicrobial peptides isolated from horseshoe crab, their derivatives or pharmaceutically acceptable salts and a β-lactam antibiotic or chloramphenicol antibiotic exhibit potent antimicrobial activities against Gram positive bacteria including MRSAs and Gram negative bacteria at low concentrations. Therefore, the compositions are useful as antimicrobial medical agents for the prevention and treatment of infections of respiratory tract, wounds and urogenital tract, and otorhinolaryngological and ophthalmological infections, and sepsis.

The compositions may be used for the prevention and treatment of stomatitis, periodontitis, dental caries and so forth caused by oral microorganisms.

The compositions are particularly effective against MRSAs at low concentrations, thus can be applied for the prevention and treatment of patients in critical condition caused by MRSA infections of deeper lying organs and opportunistic infectious diseases of immunocompromised patients due to the administration of anticancer agents or immunosuppressive agents.

Furthermore, the above mentioned compositions may be used for gargles and disinfectants for the prevention of nosocomial infections due to MRSAs from infected patients or carriers to the other hospitalized patients and members of the institute free from MRSA.

The antimicrobial compositions of the present invention can be used to prepare various pharmaceutical preparations using conventional carriers, fillers, binders, disintegrators, lubricants, sweeteners and so forth by known methods. The resultant compositions may be administered orally as solid preparations such as tablets, capsules, granules, powder preparations and troches, and liquid preparations such as syrup and elixirs. The compositions can be administered parenterally as injections, for example intravenous and intramuscular injections, or spray forms such as aerosol preparations. Furthermore, the compositions may take the forms of topical preparations such as suppositories, ointments and cataplasms.

In the compositions of the present invention, the weight ratios of the antimicrobial peptides derived from horseshoe crab, their derivatives or pharmaceutically acceptable salts and β-lactam antibiotics or chloramphenicol antibiotics are generally 1:0.5 to 1:50, but may be modified according to the properties of the antibiotics. The resultant compositions are administered preferably at doses of 0.1–100 mg/kg/day in several portions though the doses may vary with the symptoms and ages of patients. The compositions exhibit minimum inhibitory antimicrobial activities at doses of ½ or lower to those of single administration of the antimicrobial peptides derived from horseshoe crab with less toxic adverse effects.

The antimicrobial effect of the composition of the present invention will be shown by the following experiments.

(1) Isolation of MRSA

The MRSAs used for the experiments shown below were isolated as follows. Specimens of urine, sputa and pus of hospitalized patients in Nagoya University, School of Medicine Hospital were smeared and cultured on blood agar medium. *Staphylococcus aureus* was isolated and identified from the grown colonies. Their sensitivity were examined using BBL test disks containing one μg of oxacillin (BBL Microbiology System Co., Ltd.) and strains showing inhibitory zone of 10 mm or less were classified as MRSA. A total of 55 strains of MRSA Nos. 170, 199, 3-50, 3-53 and so forth were isolated. Their sensitivity were confirmed by an agar plate dilution method using Mueller-Hinton agar medium of BBL (BBL Microbiology System Co., Ltd.) containing 100, 50, 25, 12.5, 6.3, 3.2, 1.6 or 0.8 μg/ml of methicillin (Banyu Pharmaceutical Co., Ltd.).

(2) Determination of Minimum Inhibitory Concentration (MIC)

MRSAs obtained by the preceding method were cultured in L medium (1% bactotrypton, 0.5% yeast extract, 0.5% NaCl, pH 7.2) overnight and diluted 40-fold with a phosphate buffered saline solution (PBS).

Separately, tachyplesin I was diluted by 2-fold method using M9 medium (a synthetic medium added with 1% casamino acid) or T broth (0.5% bactotrypton and 0.5% NaCl) to give concentrations of 200-0.4 μg/ml and poured in a 96 well microplate at 100 μl/well each.

The 40-fold diluted bacterial solution was further diluted 10-fold with the M9 medium or T broth and poured 100 μl each to the above wells and the combined solution was mixed to give final concentration of 100-0.2 μg/ml of tachyplesin I. The bacterial concentration was made approximately $10^6$ cfu/well (cfu=colony forming unit).

The resultant mixed solutions of bacterial and tachyplesin I solutions were cultured overnight (18 hrs.) at 37° C. The growth of bacteria was determined by the turbidity of the medium and the minimum concentration required to inhibit their growth was used as the minimum inhibitory concentration (MIC). The results are shown in FIG. 1.

As shown in FIG. 1, MICs of tachyplesin I for total 55 strains were 3.2 μg/ml for seven strains (13% of total strains), 6.3 μg/ml for 47 strains (85%) and 12.5 μg/ml for one strain (2%).

(3) MICs Against MRSAs

MICs of various antimicrobial peptides derived from horseshoe crab against 55 strains of clinically isolated MRSA were determined by a similar method to that shown above. As shown in the following Table, most of the antimicrobial peptides revealed MIC of approximately 3.2 μg/ml.

| Antimicrobial peptide | MIC (μg/ml) |
| --- | --- |
| Tachyplesin I | 3.2 |
| Tachyplesin II | 3.2 |
| Polyphemusin I | 3.2 |
| Polyphemusin II | 6.3 |

The antimicrobial mechanisms of the peptides such as tachyplesins against MRSAs are supposed to be similar to those of against *Escherichia coil* and Salmonella spp. There is an energy producing mechanism by oxidative phosphorylation in cytoplasmic membrane of bacteria, which couples with membrane potential. The action mechanism against *E. coli* was modeled in artificial vesicles using inner membrane of *E. coli* and the action of tachyplesin I was investigated in vitro. It was shown that Tachyplesin I depolarized the membrane potential generated in the cytoplasmic membrane. This suggests the inhibition of production of high energy phosphate bond resulting in bactericidal effect to the cells. This mechanism also indicates that tachyplesin I has potent antimicrobial activity against Gram positive bacteria having no outer membrane as MRSAs.

(4) Synergistic Antimicrobial Activities Against MRSAs by Combinations of Tachyplesins and Antibiotics Synergistic antimicrobial activities by the combinations of tachyplesin I and β-lactam antibiotics or chloramphenicol antibiotics against above mentioned clinically isolated MRSAs were examined and the results against MRSA No. 3-50 strain are shown in the following Tables.

(i) Combinations of Tachyplesin I (TAC-I) and Cefazolin (CEZ)

TABLE 1

| CEZ (μg/ml) | TAC-I (μg/ml) | | | |
|---|---|---|---|---|
| | 0 | 0.4 | 0.8 | 1.6 |
| 0 | + | + | + | + |
| 10 | + | + | + | + |
| 20 | + | + | + | − |
| 40 | − | − | − | − |

In the Table, + shows growth − shows no growth (ii) Combinations of Tachyplesin I (TAC-I) and Ampicillin (ABPC)

TABLE 2

| ABPC (μg/ml) | TAC-I (μg/ml) | | | |
|---|---|---|---|---|
| | 0 | 0.4 | 0.8 | 1.6 |
| 0 | + | + | + | + |
| 10 | + | + | + | + |
| 20 | + | + | + | − |

(iii) Combinations of Tachyplesin I (TAC-I) and Chloramphenicol (CP)

TABLE 3

| CP (μg/ml) | TAC-I (μg/ml) | | | |
|---|---|---|---|---|
| | 0 | 0.4 | 0.8 | 1.6 |
| 0 | + | + | + | + |
| 5 | + | + | + | + |
| 10 | + | + | + | − |
| 20 | + | + | + | − |

As shown in the above Tables, concurrent administration of tachyplesin I and cefazolin, ampicillin or chloramphenicol exhibited remarkably enhanced antimicrobial effect at a concentration of 1.6 μg/ml of tachyplesin I in comparison with that of 3.2 μg/ml for single administration of tachyplesin I. Combinations of polyphemusin II and above mentioned antibiotics were also investigated and the combinations and single administrations showed MIC of 1.6 and 6.3 μg/ml, respectively. Thus marked synergistic effects in the combination of tachyplesins and the other antibiotics were confirmed.

The present invention will be explained in detail by the following examples of pharmaceutical preparations.

Example 1

| Tachyplesin I | 5 mg |
|---|---|
| Cefazolin | 95 mg |
| Lactose | 130 mg |
| Potato starch | 60 mg |
| Magnesium stearate | 10 mg |
| Total | 300 mg |

Tachyplesin I, cefazolin, lactose and potato starch were homogeneously mixed, kneaded with water and granulated with a granulater. The resultant granules were dried with a stream of warm air. The dried granules were mixed with magnesium stearate and tabletted with a tablet machine to give tablets.

Example 2

Tablets were prepared by a method similar to that of Example 1, using tachyplesin II and chloramphenicol.

Example 3

In a saline solution, 10 mg of tachyplesin I and 100 mg of cefazolin were dissolved. The resultant solution was aseptically filtered and filled in ampoules to give intravenous injection solutions.

Example 4

Intravenous injection solutions were prepared by a method similar to that of Example 3, using polyphemusin II and cefazolin.

Example 5

| Tachyplesin I | 10 mg |
|---|---|
| Ampicillin | 190 mg |
| Lactose | 120 mg |
| Total | 320 mg |

Above mentioned components were homogeneously mixed and filled in hard capsules to give a capsule preparation.

Example 6

Capsule preparations were prepared by a similar method with that of Example 5, using polyphemusin I and cefazolin.

We claim:

1. A pharmaceutical composition comprising a synergistic combination of an antimicrobial peptide, or a pharmaceutically acceptable salt thereof, and an antibiotic, wherein in said composition:

(a) the ratio (by weight) of said peptide to said antibiotic is in the range of about 0.02 to 2;

(b) said peptide is isolated from horseshoe crab hemocytes and is selected from the group consisting of tachyplesin I, tachyplesin II, tachyplesin III, polyphemusin I, polyphemusin II, and gigasin II; and (c) said antibiotic is selected from the group consisting of cefazolin, ampicillin, and chloramphenicol.

2. A pharmaceutical composition comprising a synergistic combination of an antimicrobial peptide, or a pharmaceutically acceptable salt thereof, and an antibiotic, wherein in said composition:

(a) the ratio (by weight) of said peptide to said antibiotic is in the range of about 0.02 to 2;

(b) said peptide is selected from the group consisting of tachyplesin I, tachyplesin II, tachyplesin III, polyphemusin I, polyphemusin II, or gigasin II in which one or more conservative amino acid substitutions have been made; and (c) said antibiotic is selected from the group consisting of cefazolin, ampicillin, and chloramphenicol.

3. A pharmaceutical composition comprising a synergistic combination of an antimicrobial peptide, or a pharmaceutically acceptable salt thereof, and an antibiotic, wherein in said composition:

(a) the ratio (by weight) of said peptide to said antibiotic is in the range of about 0.02 to 2;

(b) said peptide is selected from the group consisting of tachyplesin I, tachyplesin II, tachyplesin III, polyphemusin I, polyphemusin II, or gigasin II which bear one or more additional amino acid residues at the N- or C-terminus; and (c) said antibiotic is selected from the group consisting of cefazolin, ampicillin, and chloramphenicol.

4. A method of inhibiting growth of methicillin-resistant *Staphylococcus areus* in vitro comprising contacting said methicillin-resistant *Staphylococcus areus* with a synergistic combination of an antimicrobial peptide, or a pharmaceutically acceptable salt thereof, and an antibiotic, wherein said peptide is selected from the group consisting of tachyplesin I, tachyplesin II, tachyplesin III, polyphemusin I, polyphemusin II, and gigasin II and wherein said antibiotic is selected from the group consisting of cefazolin, ampicillin, and chloramphenicol.

5. A method of inhibiting growth of methicillin-resistant *Staphylococcus areus* in a mammal infected therewith comprising administering to said mammal a composition comprising a synergistic combination of an antimicrobial peptide, or a pharmaceutically acceptable salt thereof, and an antibiotic, wherein said peptide is selected from the group consisting of tachyplesin I, tachyplesin II, tachyplesin III, polyphemusin I, polyphemusin II, and gigasin II and wherein said antibiotic is selected from the group consisting of cefazolin, ampicillin, and chloramphenicol.

6. A method of treating a mammal infected with methicillin-resistant *Staphylococcus areus* comprising administering to said mammal a composition comprising a synergistic combination of an antimicrobial peptide, or a pharmaceutically acceptable salt thereof, and an antibiotic, wherein said peptide is selected from the group consisting of tachyplesin I, tachyplesin II, tachyplesin II, polyphemusin I, polyphemusin II and gigasin II in which one or more conservative amino acid substitutions have been made; and said antibiotic is selected from the group consisting of cefazolin, ampicillin and chloramphenicol.

7. A method of treating a mammal infected with methicillin-resistant *Staphylococcus areus* comprising administering to said mammal a composition comprising a synergistic combination of an antimicrobial peptide, or a pharmaceutically acceptable salt thereof, and an antibiotic, wherein said peptide is selected from the group consisting of tachyplesin I, tachyplesin II, tachyplesin II, polyphemusin I, polyphemusin II and gigasin II which bear one or more additional amino acid residues at the N- or C-terminus; and said antibiotic is selected from the group consisting of cefazolin, ampicillin and chloramphenicol.

8. The pharmaceutical composition of claim 1, 2 or 3 for inhibiting microbes comprising:

(a) tachyplesin I at a concentration of at least 1.6 µg/ml; and (b) cefazolin at a concentration of at least 20 µg/ml.

9. The pharmaceutical composition of claim 1, 2 or 3 for inhibiting microbes comprising:

(a) tachyplesin I at a concentration of at least 1.6 µg/ml; and (b) ampicillin at a concentration of at least 20 µg/ml.

10. The pharmaceutical composition of claim 1, 2 or 3 for inhibiting microbes comprising:

(a) tachyplesin I at a concentration of at least 1.6 µg/ml; and (b) chloramphenicol at a concentration of at least 10 µg/ml.

11. The composition of claim 2 or 3 wherein said peptide is obtained by synthetic or recombinant methods.

12. The method of claim 4, 5, 6 or 7 wherein said peptide is obtained by synthetic or recombinant methods.

* * * * *